(12) United States Patent
Weiss et al.

(10) Patent No.: US 9,616,001 B2
(45) Date of Patent: Apr. 11, 2017

(54) SOLID LIPID NANOPARTICLES (I)

(71) Applicant: DSM IP ASSETS B. V., Heerlen (NL)

(72) Inventors: Jochen Weiss, Basel (CH); Christiane Schweiggert, Basel (CH); Bruno Leuenberger, Basel (CH); Markus Novotny, Basel (CH); Concetta Tedeschi, Basel (CH); Anne Kessler, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/775,020

(22) PCT Filed: Mar. 14, 2014

(86) PCT No.: PCT/EP2014/055088
§ 371 (c)(1),
(2) Date: Sep. 11, 2015

(87) PCT Pub. No.: WO2014/140264
PCT Pub. Date: Sep. 18, 2014

(65) Prior Publication Data
US 2016/0022550 A1     Jan. 28, 2016

(30) Foreign Application Priority Data

Mar. 15, 2013 (EP) .................... 13159490

(51) Int. Cl.
| | |
|---|---|
| *A61K 8/02* | (2006.01) |
| *A61K 8/24* | (2006.01) |
| *A61K 8/31* | (2006.01) |
| *A61K 8/67* | (2006.01) |
| *A61K 8/37* | (2006.01) |
| *A61K 8/97* | (2006.01) |
| *A61K 8/55* | (2006.01) |

(Continued)

(52) U.S. Cl.
CPC .......... *A61K 8/0241* (2013.01); *A23K 20/158* (2016.05); *A23L 29/10* (2016.08); *A23P 10/30* (2016.08); *A61K 8/24* (2013.01); *A61K 8/31* (2013.01); *A61K 8/37* (2013.01); *A61K 8/553* (2013.01); *A61K 8/671* (2013.01); *A61K 8/97* (2013.01); *A61Q 19/00* (2013.01); *A23V 2002/00* (2013.01); *A61K 2800/10* (2013.01); *A61K 2800/413* (2013.01); *A61K 2800/52* (2013.01); *A61K 2800/651* (2013.01); *A61K 2800/652* (2013.01); *A61K 2800/654* (2013.01)

(58) Field of Classification Search
CPC ..... A23K 20/158; A23L 1/0029; A23L 1/035; A23V 2002/00; A61K 2800/10; A61K 2800/413; A61K 2800/52; A61K 2800/651; A61K 2800/652; A61K 2800/654; A61K 8/0241; A61K 8/24; A61K 8/31; A61K 8/37
See application file for complete search history.

(56) References Cited

FOREIGN PATENT DOCUMENTS

WO    WO 2013/051994    4/2013

OTHER PUBLICATIONS

International Search Report for PCT/EP2014/055088, mailed Apr. 24, 2014, 3 pages.

(Continued)

*Primary Examiner* — Aradhana Sasan
(74) *Attorney, Agent, or Firm* — Nixon & Vanderhye P.C.

(57) ABSTRACT

The present invention relates to new (foodgrade) solid lipid nanoparticles, as well as the production of such solid lipid nanoparticles and the use of them.

8 Claims, 2 Drawing Sheets

(51) Int. Cl.
*A61Q 19/00* (2006.01)
*A23K 20/158* (2016.01)
*A23P 10/30* (2016.01)
*A23L 29/10* (2016.01)

(56) References Cited

OTHER PUBLICATIONS

Neves et al., Nanotechnology-based systems for the treatment and prevention of HIV/AIDS, *Advanced Drug Delivery Reviews*, vol. 62, No. 4-5, Mar. 18, 2010, pp. 458-477.
Behboudi et al., Quillaja saponin formulations that stimulate proinflammatory cytokines elicit a potent acquired cell-mediated immunity, *Scandinavian Journal of Immunology*, vol. 50, No. 4, Oct. 1, 1999, pp. 371-377.
Database WPI, Week 200879, Thomson Scientific, XP 002722915, 1 page.
Database WPI, Week 200357, Thomson Scientific, XP 002722916, 1 page.

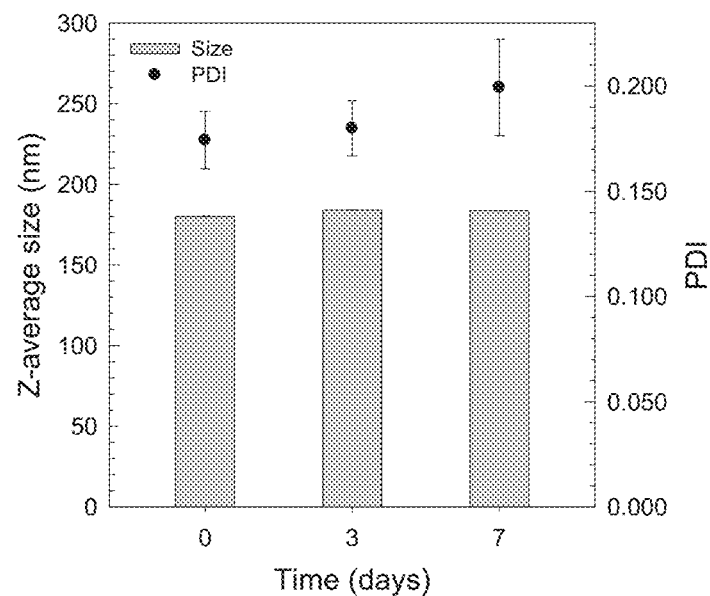
FIG. 1A  SLN formulation with β-carotene
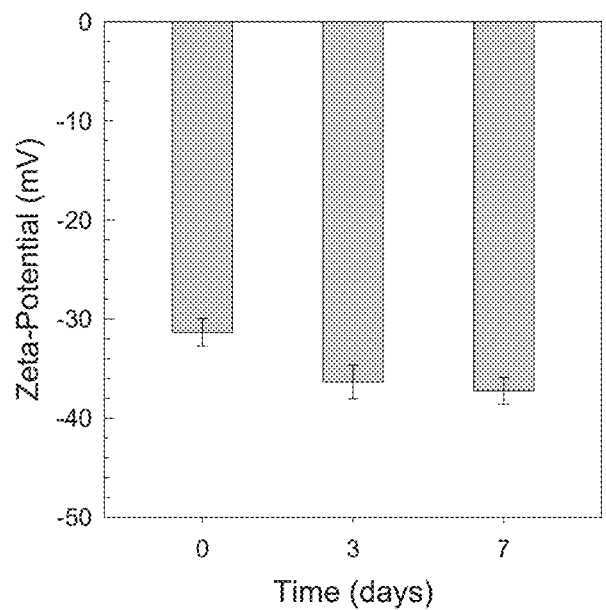
FIG. 1B  SLN formulation with β-carotene

SOLID LIPID NANOPARTICLES (I)

This application is the U.S. national phase of International Application No. PCT/EP2014/055088 filed 14 Mar. 2014, which designated the U.S. and claims priority to EP Patent Application No. 13159490.5 filed 15 Mar. 2013, the entire contents of each of which are hereby incorporated by reference.

FIELD

The present invention relates to new (foodgrade) solid lipid nanoparticles, as well as the production of such solid lipid nanoparticles and the use of them.

BACKGROUND AND SUMMARY

Solid lipid nanoparticles (SLNs) are for example used as a novel approach for oral as well as for parenteral lipophilic or amphiphilic active ingredients delivery. Today the most common way for such delivery are emulsions.

SLN are suitable for such a use due to several important advantages such as
  (i) incorporation of lipophilic as well as amphiphilic active ingredients, and
  (ii) no biotoxicity, and
  (iii) avoidance of organic solvents, and
  (iv) possibility of controlled active ingredients release, and
  (v) excellent stability (mechanical and chemical), and
  (vi) usable for spray-drying, and
  (vii) good optical properties (allows the production of non-turbid formulations), and
  (viii) sterilisable.

SLNs have a (more or less) spherical shape with a diameter of 10-1000 nm. In case non-turbid formulation are to be produced, then the diameter of the SLNs should be between 50-300 nm.

SLNs possess a solid lipid core which is stabilized by emulsifiers.

SLNs are known from the prior art such as Mehnert et al., Adv. Drug Del. Rev. 47 (2001), 165-196.

The lipid phase (lipid core) of the SLN is in a solid state (aka crystallized). This phase may comprise lipophilic and/or amphiphilic active ingredients (such as antimicrobial, antioxidants, polyphenols, vitamins, poly unsaturated fatty acids (PUFAs), dyestuffs, etc), which are (if they are included in the solid state) protected from degradation.

This is a very important further advantage which allows to prolonging the shelf life of lipophilic or amphiphilic active ingredients in a sophisticated way.

Crystallized lipids can form usually three different kinds of crystals:
  $\alpha$, $\beta'$, and $\beta$ crystals.

The $\alpha$-crystal chains have hexagonal arrangement, with the shortest spacing line in X-ray diffraction pattern. Furthermore, this crystal type has the least densely packed lipid structure and it melts at temperatures below that of the other crystals.

The $\beta'$-crystals are the transition form between $\alpha$- and $\beta$-crystals, and they are orthorhombic. They are more ordered than $\alpha$-crystals and melt at higher temperatures.

The $\beta$-crystals are packed in triclinic arrangement and have highly ordered platelet-like structures. They are the most stable form, and therefore they melt at the highest temperature. Due to kinetic reasons the crystals rearrange themselves from less ordered $\alpha$-crystals to highly ordered $\beta$-crystals implying a shape change from spherical to plated shaped particles (Bunjes, Steiniger, & Richter, 2007). From this it follows, that the oil-water surface area increases leading to aggregation and gel formation of hydrophobic patches.

But in order to include a bioactive ingredient into the lipid core of the SLN, without incurring the above mentioned phase separation the unstable $\alpha$ and/or $\beta'$-crystal structure is preferred.

The goal of the present invention is to find a way to provide SLN with a $\alpha$ and/or $\beta'$-crystal structure which is stable and therefore does not polymorph into the $\beta$ crystal structure. The SLN must be (storage) stable for weeks.

Surprisingly, it was found that when a specific emulsifier was used (which is at least one saponin), then a stable SLN wherein the solid lipid has a $\alpha$ and/or $\beta'$-crystal structure is obtained.

Therefore the present invention relates to solid lipid nanoparticles (I) comprising
  (a) a core comprising
    (i) a lipid phase in a solid state, and
    (ii) optionally at least one lipophilic and/or amphiphilic active ingredient, and
  (b) an emulsifier system comprising
    (i) at least one emulsifier
characterised in
that the emulsifier system comprises at least one saponin.

Furthermore it is preferred that the emulsifier system of the SLN has a crystallization point which is lower than the crystallization point of the core of the SLN. That means that the emulsifier system should crystallize before the core crystallizes.

Therefore the present invention also relates to solid lipid nanoparticles (II), which are solid lipid nanoparticles (I), wherein the emulsifier system has a crystallization point which is lower than the crystallization point of the core.

The lipid phase can be any oil (mixture of oils), which is solid at the storage temperature of the SLN. Suitable oils are for example triglycerides, partial glycerides, fatty acids, steroids and waxes.

Therefore the present invention also relates to solid lipid nanoparticles (III), which are solid lipid nanoparticles (I) or (II), wherein the lipid phase is an oil (mixture of oils), which is solid at the storage temperature of the SLN. Suitable oils are for example triglycerides, partial glycerides, fatty acids, steroids and waxes.

Therefore the present invention also relates to solid lipid nanoparticles (III'), which are solid lipid nanoparticles (I), (II) or (III), wherein the lipid phase is an oil (mixture of oils) chosen from the group consisting of triglycerides, partial glycerides, fatty acids, steroids and waxes.

The lipophilic and/or amphiphilic active ingredient can be for example an antimicrobial, an antioxidant, a polyphenol, a vitamin, a PUFA or a dyestuff, as well as mixtures of such ingredients.

Therefore the present invention also relates to solid lipid nanoparticles (IV), which are solid lipid nanoparticles (I), (II), (III) or (III'), wherein the lipophilic and/or amphiphilic active ingredient is chosen from the group consisting of antimicrobial, an antioxidant, a polyphenol, a vitamin, a PUFA or a dyestuff, as well as mixtures of such ingredients.

BRIEF DESCRIPTION OF THE DRAWINGS

FIGS. 1A and 1B are bar graphs, wherein FIG. 1A is a graph of the mean particle size (nm) and polydispersity index (PDI) versus time (days), and FIG. 1B is a graph of the zeta-potential of SLN (10% tristearin, 1.5% hydrogenated lecithin, 1.5% *Quillaja* extract in 10 mM sodium phosphate buffer, pH 7) formulated with β-carotene (5 mg) during 7 days of storage at room temperature, wherein the mean and standard deviation were calculated from one sample with 3 measurements for size and PDI (n=3), and 4 measurements for zeta-potential (n=4), and FIGS. 2A and 2B are bar graphs wherein FIG. 2A is a graph of the mean particle size (nm) and polydispersity index (PDI) versus time (days), and FIG. 1B is a graph of the zeta-potential of SLN (10% tristearin, 1.5% hydrogenated lecithin, 1.5% *Quillaja* extract in 10 mM sodium phosphate buffer, pH 7) formulated with Vitamin A (5 mg) during 7 days of storage at room temperature, wherein the mean and standard deviation were calculated from one sample with 3 measurements for size and PDI (n=6), and 4 measurements for zeta-potential (n=8).

DETAILED DESCRIPTION

Figure 2A:
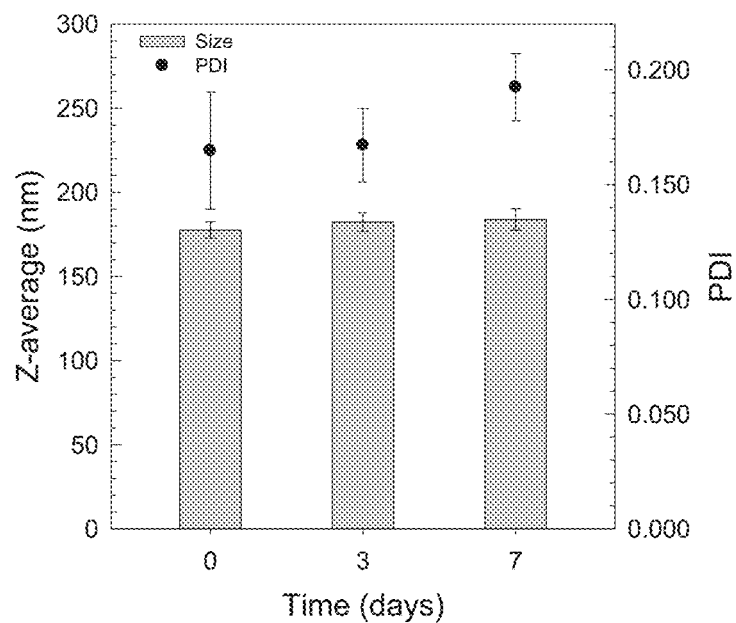
Figure 2B:
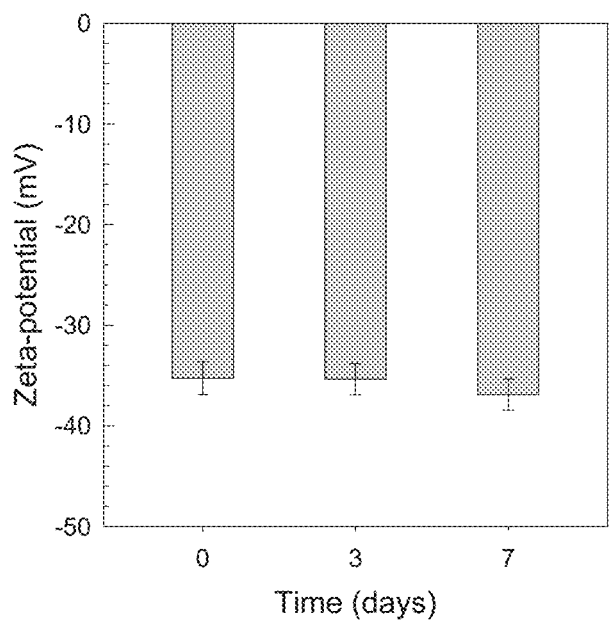

Saponins are amphipathic glycosides grouped, in terms of phenomenology, by the soap-like foaming they produce when shaken in aqueous solutions, and, in terms of structure, by their composition of one or more hydrophilic glycoside moieties combined with a lipophilic triterpene derivative.

Saponins have historically been understood to be plant-derived, but they have also been isolated from marine organisms. Saponins are indeed found in many plants, and derive their name from the soapwort plant (genus *Saponaria*, family Caryophyllaceae), the root of which was used historically as a soap.

Saponins are also found in the botanical family Sapindaceae, with its defining genus *Sapindus* (soapberry or soapnut), and in the closely related families Aceraceae (maples) and Hippocastanaceae (horse chestnuts; ref. needed).

It is also found heavily in *Gynostemma pentaphyllum* (*Gynostemma*, Cucurbitaceae) in a form called gypenosides, and ginseng or red ginseng (*Panax*, Araliaceae) in a form called ginsenosides. Within these families, this class of chemical compounds is found in various parts of the plant: leaves, stems, roots, bulbs, blossom and fruit.

Commercial formulations of plant-derived saponins, e.g., from the soap bark (or soapbark) tree, *Quillaja saponaria*.

Saponins are commercially available for example from Desert King International and National Starch.

A preferred saponin compound in the context of the present invention is *quillaja saponaria* (E999). The E numbers (i.e. E999) are codes for chemicals which can be used as food additives for use within the European Union and Switzerland (the "E" stands for "Europe").

Therefore the present invention also relates to solid lipid nanoparticles (V), which are solid lipid nanoparticles (I), (II), (III), (III') or (IV), wherein the saponin is *quillaja saponaria*.

The emulsifier system of the embodiment of the present invention can also comprise other emulsifier(s) (=co-emulsifiers). In case such one or more co-emulsifers are used, the emulsifier system should still crystallise before the core crystallises.

Suitable co-emulsifiers are i.e. polysorbates (polysorbates are oily liquids derived from PEG-ylated sorbitan (a derivative of sorbitol) esterified with fatty acids), such as Polysorbate 40 (polyoxyethylene (20) sorbitan monopalmitate), Polysorbate 60 (polyoxyethylene (20) sorbitan monostearate) and Polysorbate 80 (polyoxyethylene (20) sorbitan monooleate);

Phospholipids, such as phosphatidic acid (phosphatidate), phosphatidylethanolamine (cephalin). phosphatidylcholine (lecithin), hydrogenated lecithin, phosphatidylserine, phosphatidylinositol phosphate, phosphatidylinositol bisphosphate, phosphatidylinositol triphosphate, ceramide phosphorylcholine (Sphingomyelin), ceramide phosphorylethanolamine (Sphingomyelin) and ceramide phosphorylglycerol;

stearoyl-2-lactylate such as sodium-stearoyl-2-lactylate (E 481); and citric acid ester of mono- and di-glycerides, preferably Citric acid esters of mono and diglycerides of fatty acids (E472c).

Therefore the present invention also relates to solid lipid nanoparticles (VI), which are solid lipid nanoparticles (I), (II), (III), (III'), (IV) or (V), wherein the emulsifier system comprises at least one co-emulsifier.

Therefore the present invention also relates to solid lipid nanoparticles (VI'), which are solid lipid nanoparticles (I), (II), (III), (III'), (IV), (V) or (VI), wherein the emulsifier system comprises at least one co-emulsifier chosen from the group consisting of polysorbates, phospholipids, stearoyl-2-lactylate and citric acid ester of mono- and di-glycerides.

Therefore the present invention also relates to solid lipid nanoparticles (VI"), which are solid lipid nanoparticles (I), (II), (III), (III'), (IV), (V), (VI) or (VI'), wherein the emulsifier system comprises at least one co-emulsifier chosen from the group consisting of Polysorbate 40 (polyoxyethylene (20) sorbitan monopalmitate), Polysorbate 60 (polyoxyethylene (20) sorbitan monostearate), Polysorbate 80 (polyoxyethylene (20) sorbitan monooleate), phosphatidic acid (phosphatidate), phosphatidylethanolamine (cephalin). phosphatidylcholine (lecithin), hydrogenated lecithin, phosphatidylserine, phosphatidylinositol phosphate, phosphatidylinositol bisphosphate, phosphatidylinositol triphosphate, ceramide phosphorylcholine (Sphingomyelin), ceramide phosphorylethanolamine (Sphingomyelin), ceramide phosphorylglycerol, stearoyl-2-lactylate and citric acid ester of mono- and di-glycerides.

Therefore the present invention also relates to solid lipid nanoparticles (VI'''), which are solid lipid nanoparticles (I), (II), (III), (III'), (IV), (V), (VI) or (VI'), wherein the emulsifier system comprises at least one co-emulsifier chosen from the group consisting of lecithin, hydrogenated lecithin, sodium-stearoyl-2-lactylate (E 481) and citric acid esters of mono and diglycerides of fatty acids (E472c).

The concentration of the at least one saponin is 0.1-30 weight-% (wt-%), based on the total weight of the SLN, preferably 0.5-20 wt-%.

Therefore the present invention also relates to solid lipid nanoparticles (VII), which are solid lipid nanoparticles (I), (II), (III), (III'), (IV), (V), (VI), (VI'), (VI") or (VI'''), wherein the concentration of the at least one saponin is 0.1-30 weight-% (wt-%), based on the total weight of the SLN.

Therefore the present invention also relates to solid lipid nanoparticles (VII'), which are solid lipid nanoparticles (I), (II), (III), (III'), (IV), (V), (VI), (VI'), (VI") or (VI'''), wherein the concentration of the at least one saponin is 0.5-20 wt-%.

The concentration of the at least co-emulsifier is 0.1-30 wt-%, based on the total weight of the SLN, preferably 0.5-20 wt-%.

Therefore the present invention also relates to solid lipid nanoparticles (VIII), which are solid lipid nanoparticles (I), (II), (III), (III'), (IV), (V), (VI), (VI'), (VI"); (VI'''), (VII) or (VII'), wherein the concentration of the at least co-emulsifier is 0.1-30 wt-%, based on the total weight of the SLN.

Therefore the present invention also relates to solid lipid nanoparticles (VIII'), which are solid lipid nanoparticles (I), (II), (III), (III'), (IV), (V), (VI), (VI'), (VI"); (VI'''), (VII) or (VII'), wherein the concentration of the at least co-emulsifier is 0.5-20 wt-%.

The concentration of the lipophilic and/or amphiphilic active ingredient can be up to 60 wt-%, based on the total amount of the SLN.

Therefore the present invention also relates to solid lipid nanoparticles (IX), which are solid lipid nanoparticles (I), (II), (III), (III'), (IV), (V), (VI), (VI'), (VI"); (VI'''), (VII), (VII'), (VIII) or (VIII'), wherein the concentration of the lipophilic and/or amphiphilic active ingredient is up to 60 wt-%, based on the total amount of the SLN.

The SLN can be prepared according to methods known from the prior art. For example preparation methods at elevated temperatures (above the melting temperature of the lipid) such as hot homogenization and hot microemulsification, and there are methods at room temperature or below (i.e. below the melt temperature of the lipids), such as milling techniques (Kakran, et al., 2012; R. H. Müller, Gohla, & Keck, 2011; Rainer H. Müller, et al., 2000).

Preferably SLNs according to the present invention are produced by using hot homogenisation.

Therefore the present invention also relates to a process of production of solid lipid nanoparticles (IX), which are solid lipid nanoparticles (I), (II), (III), (III'), (IV), (V), (VI), (VI'), (VI"); (VI'''), (VII), (VII'), (VIII), (VIII') or (IX), characterised in that the process is a hot homogenisation process.

The SLNs according to the present invention can be used in various fields of application. The field of application usually depends on the lipophilic and/or amphiphilic active ingredient, which are incorporated.

The SLNs can be used as such or they can be used for the production of food products, feed products or personal care products.

Therefore, a further embodiment of the present invention relates to the use of the solid lipid nanoparticles (I), (II), (III), (III'), (IV), (V), (VI), (VI'), (VI"); (VI'''), (VII), (VII'), (VIII), (VIII') or (IX) in the production of food products, feed products or personal care products.

The amount of SLN (and the lipophilic and/or amphiphilic active ingredients) in such products depends on the kind of product and the lipophilic and/or amphiphilic active ingredients.

Furthermore the present invention also relates to of food products, feed products and personal care products comprising solid lipid nanoparticles (I), (II), (III), (III'), (IV), (V), (VI), (VI'), (VI"); (VI'''), (VII), (VII'), (VIII), (VIII') or (IX).

The invention is illustrated by the following Examples. All temperatures are given in ° C. and all parts and percentages are related to the weight.

Example 1

0.6 wt-% of *Quillaja* Extract Solution

A 50 g sample weight, of this example consists of 90 wt-% surfactant (*Quillaja* extract, 0.6 wt-%)/sodium phosphate buffer solution (10 mM, pH=7) and 10 wt-% glyceryl tripalmitate. The glyceryl tripalmitate was heated to 85° C. to fully melt the lipid. After heating separately the surfactant buffer solution at the same temperature (85° C.), the lipid melt and the surfactant aqueous phase were mixed together and stirred for one minute by using a homogenizer standard unit (Labworld-online, Staufen, Germany). The content of *Quillaja* extract was 0.54 w-%, based on the total weight of the sample. The so-formed hot premix was directly homogenized by passing the emulsion 5 times at 10.000 psi (≈700 bar) through a high pressure homogenizer (EmulsiFlex-C3, Avestin Inc., Ottawa, Canada). Prior to homogenization the high-pressure homogenizer was heated up by cycling 5 times boiling water through the machine, to prevent emulsion crystallization. During homogenization the already homogenized sample was collected in a flask, which was located in a water-bath. The fine emulsion was then divided in two parts, which were stored in an ice bath for one hour to induce fat crystallization. Afterwards, the two dispersion portions were stored at 7, or 25° C., respectively.

Example 2

3.6 wt-% of *Quillaja* Extract Solution

Example 2 done in analogy to Example 1 with the exception that the content of *Quillaja* extract was increased to 3.24 wt-%, based on the total weight of the sample.

Example 3

2.4 wt-% Phosphatidylcholine with 0.6 wt-% *Quillaja* Extract

Example 3 done in analogy to Example 1 with the exception that the surfactant solution contains a mixture of Phosphatidylcholine and *Quillaja* extracts in a 4:1 ratio, respectively. The content of the total amount of surfactant being 2.7 wt-% (being the one of *Quillaja* 0.54 wt-% and of Phosphatidylcholine 2.16 wt-%) based on the total weight of the sample.

Storage Stabilities of Examples 1-3

The physical stability of all samples described in examples 1-3 was measured over a period of 3 weeks (at 7° C.).

After 3 weeks of storage, all the samples were still homogenous and fluid. No gelation, aggregation, or sedimentation was observed.

Example 4

0.005 wt-% β-Carotene

A 3.3% surfactant-cosurfactant aqueous solution was prepared mixing 1.5 g of 80H Phospholipon lecithin and 1.5 g of *Quillaja* extract in 87 g of 10 mM sodium phosphate buffer solution (pH=7). The so-produced surfactant solution was heated to 85° C. for 30 minutes in a shaking water bath. Separately, 10 g of glycerol tristearate were heated to 85° C. to fully melt the lipid and 0.005 g of β-carotene active were added to the lipid melt that was sealed and stirred (200 rpm) in the dark at 80° C. for 30-60 minutes to allow the active dissolution. The hot lipid phase was mixed with the aqueous surfactant solution held at 80° C. and stirred by a homogenizer standard unit for 2 minutes at 24000 $min^{-1}$ to produce a coarse emulsion. The content of both *Quillaja* extract and lecithin was 1.5 wt-%, based on the total weight of the sample. The hot premix was then homogenized using a Microfluidizer (H-chamber, 500 bar, 4 cycles) to create the final emulsion. The microfluidizer and chamber were heated with hot water prior to homogenization to prevent crystallization of the emulsion. The collected fine emulsion was stored in an ice bath for one hour to induce fat crystallization. Afterwards, the dispersion was stored in the dark at room temperature. The content of the encapsulated β-carotene in the SLN was 0.005 wt-%, based on the total weight of the sample.

Example 5

0.005 wt-% Vitamin A Acetate

The same conditions as in Example 4 were used, only a different active was employed. Vitamin A acetate, was processed in the same way of β-carotene Storage Stabilities of Example 4 and 5

The physical stability of the samples described in example 4 and 5 was measured over a period of 3 weeks (at 7° C. and 25° C.).

After 3 weeks of storage, all the samples were still homogenous and fluid. No gelation, aggregation, or sedimentation was observed.

The invention claimed is:

1. Solid lipid nanoparticles comprising
   (a) a core comprising,
      (a1) a lipid phase in a solid state, and
      (a2) up to 60 wt-%, based on the total weight of the solid lipid nanoparticles, of at least one lipophilic and/or amphiphilic active ingredient, and
   (b) an emulsifier system comprising:
      (b1) at least one emulsifier;
      (b2) 0.1-30 wt-%, based on the total weight of the solid lipid nanoparticles, of at least one co-emulsifier selected from the group consisting of polysorbates, phospholipids, stearoyl-2-lactylat and citric ester of mono and di-glycerides, and
      (b3) 0.1-30 wt. %, based on the total weight of the solid lipid nanoparticles, of at least one saponin compound, wherein
   the solid lipid nanoparticles are substantially spherical with a diameter of 50-300 nm.

2. The solid lipid nanoparticles according to claim 1, wherein the emulsifier system has a crystallization point which is lower than a crystallization point of the core.

3. The solid lipid nanoparticles according to claim 1, wherein the lipid phase is at least one oil selected from the group consisting of triglycerides, partial glycerides, fatty acids, steroids and waxes.

4. The solid lipid nanoparticles according to claim 1, wherein the lipophilic and/or amphiphilic active ingredient is selected from the group consisting of antimicrobials, antioxidants, polyphenols, vitamins, polyunsaturated fatty acids (PUFAs) and dyestuffs.

5. The solid lipid nanoparticles according to claim 1, wherein the saponin is *Quillaia saponaria*.

6. The solid lipid nanoparticles according to claim 1 wherein the at least one saponin is present in a concentration of 0.5-20 wt-%, based on the total weight of the solid lipid nanoparticles.

7. The solid lipid nanoparticles according to claim 1, wherein the at least one co-emulsifier is present in a concentration of 0.5-20 wt-%, based on the total weight of the solid lipid nanoparticles.

8. A food product, feed product or personal care product comprising the solid lipid nanoparticles as claimed in claim 1.

* * * * *